United States Patent [19]

Nichols et al.

[11] Patent Number: 4,995,863

[45] Date of Patent: * Feb. 26, 1991

[54] CATHETER WITH SLIT VALVE

[75] Inventors: Colin J. Nichols, Fruit Heights; Gregory N. Nordgren, West Valley City; Harvey R. Moorehead, Salt Lake City, all of Utah

[73] Assignee: Catheter Technology Corporation, Salt Lake City, Utah

[ * ] Notice: The portion of the term of this patent subsequent to Jun. 28, 2005 has been disclaimed.

[21] Appl. No.: 160,473

[22] Filed: Feb. 25, 1988

Related U.S. Application Data

[63] Continuation of Ser. No. 915,474, Oct. 6, 1986, Pat. No. 4,753,640.

[51] Int. Cl.[5] .................................... A61M 5/00
[52] U.S. Cl. ........................... 604/247; 604/9
[58] Field of Search ............ 128/658; 604/43-45, 604/164, 168, 170, 247, 280-284, 9; 137/493, 847, 848, 849

[56] References Cited

U.S. PATENT DOCUMENTS

| | | | |
|---|---|---|---|
| Re. 31,873 | 4/1985 | Howes | 128/674 |
| 2,393,003 | 1/1946 | Smith | 128/349 |
| 3,020,913 | 2/1962 | Heyer | 128/350 |
| 3,128,769 | 4/1964 | Scislowicz | 128/348 |
| 3,308,819 | 3/1967 | Arp | 604/164 |
| 3,885,561 | 5/1975 | Cami | 128/214 |
| 4,072,146 | 2/1978 | Howes | 128/2.05 D |
| 4,214,593 | 7/1980 | Imbrace et al. | 604/45 |
| 4,434,810 | 3/1984 | Atkinson | 137/493 |
| 4,475,898 | 10/1984 | Brodner et al. | 604/9 |
| 4,529,399 | 7/1985 | Groshong et al. | 604/53 |
| 4,547,194 | 10/1985 | Moorehead | 604/283 |
| 4,549,879 | 10/1985 | Groshong et al. | 604/247 |

Primary Examiner—Max Hindenburg
Attorney, Agent, or Firm—Workman, Nydegger & Jensen

[57] ABSTRACT

Catheter tubes of elastomeric material having novel lumen shapes which prevent occlusion and accommodate continued liquid flow even when kinked. Also, catheter tube slit valves are disclosed, the walls of which are not chemically weakened. Symmetrical and asymmetrical versions of said slit valves are disclosed. Combinations of highly reliable slit valves and catheter tubes are disclosed. Independently operable multilumen catheter assemblies of synthetic material, such as silicone rubber are disclosed, wherein the distal end of each lumen is normally closed by a three-position slit valve formed in a catheter tube covering. Multi-lumen catheters, and related methods, are also disclosed wherein the lumens are internal at the proximal and distal ends of the catheter tube but comprise separate tubes in between whereby, following placement of the distal end of the catheter tube in the body cavity of a patient, the unified proximal end of the tube is manipulated, sometimes subcutaneously, with the ultimately exposed tubes being thereafter severed and each equipped with a hub at a convenient exposed body site for selective independent passage of influent and effluent liquid along each lumen.

56 Claims, 6 Drawing Sheets

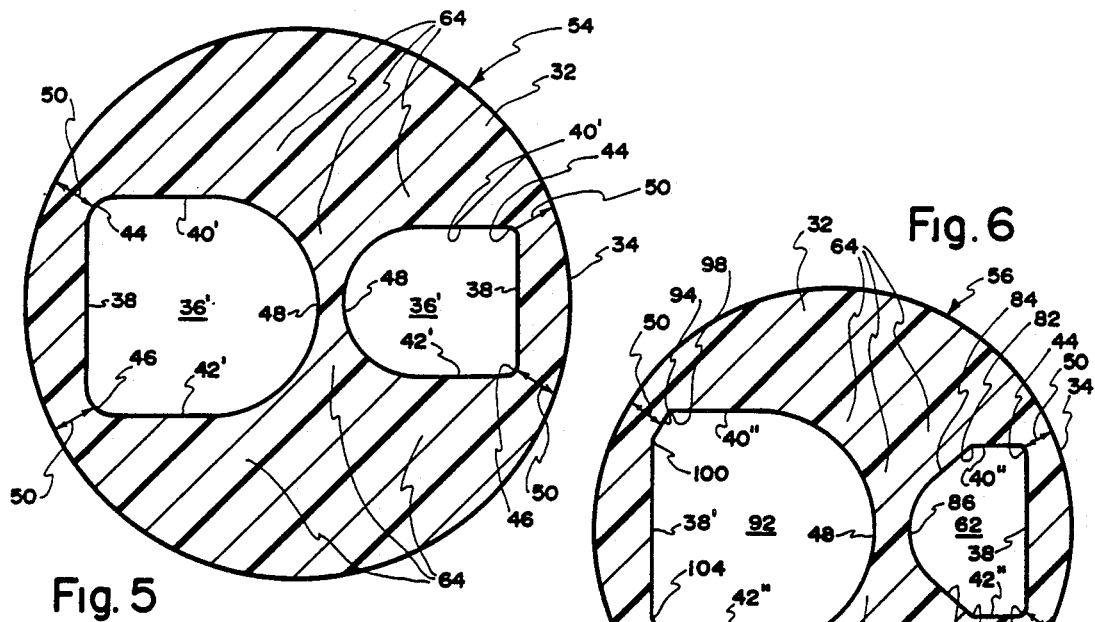
Fig. 5
Fig. 6
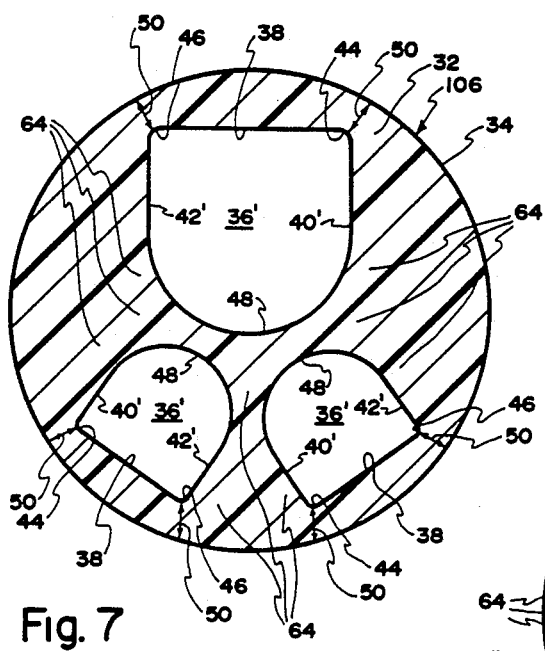
Fig. 7
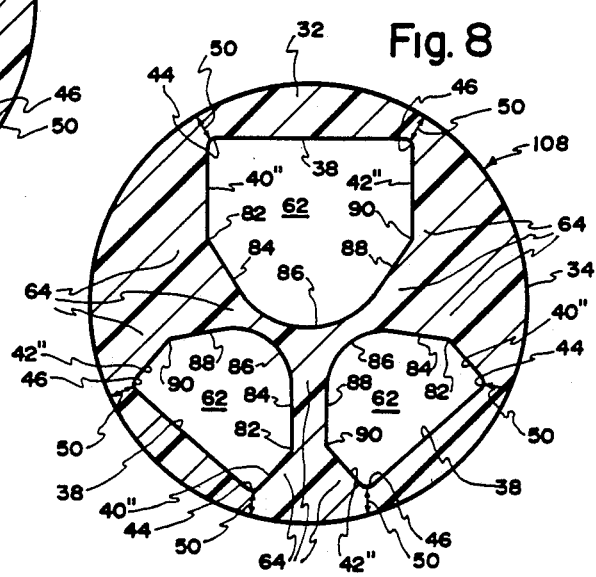
Fig. 8

Fig. 14
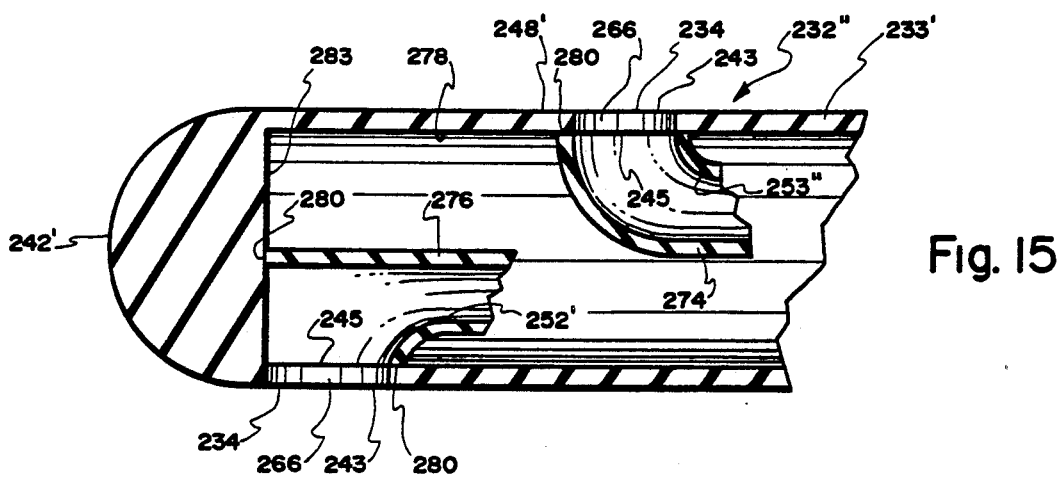
Fig. 15
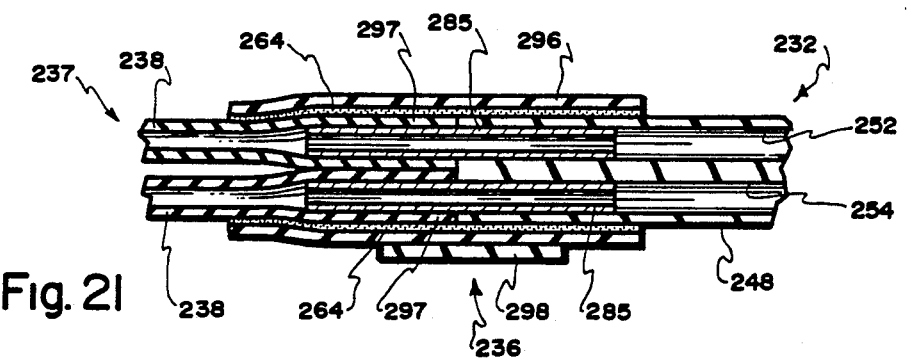
Fig. 21
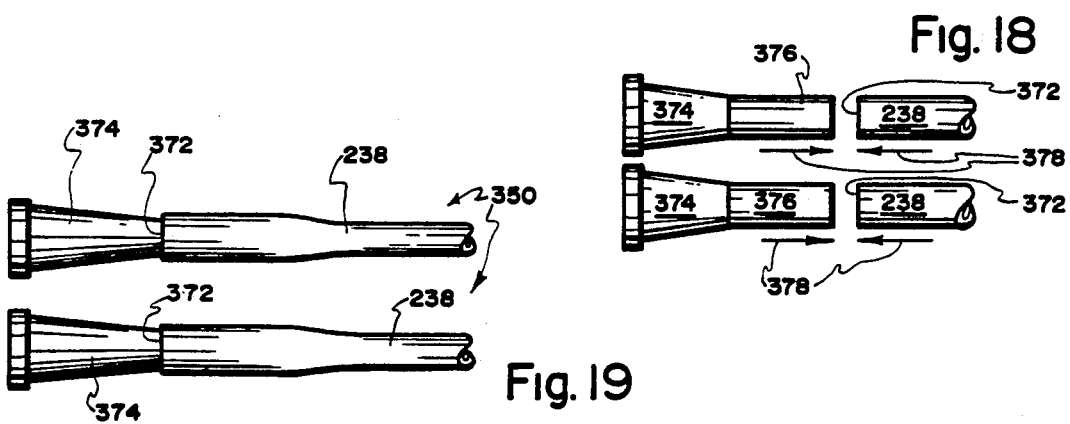
Fig. 18
Fig. 19

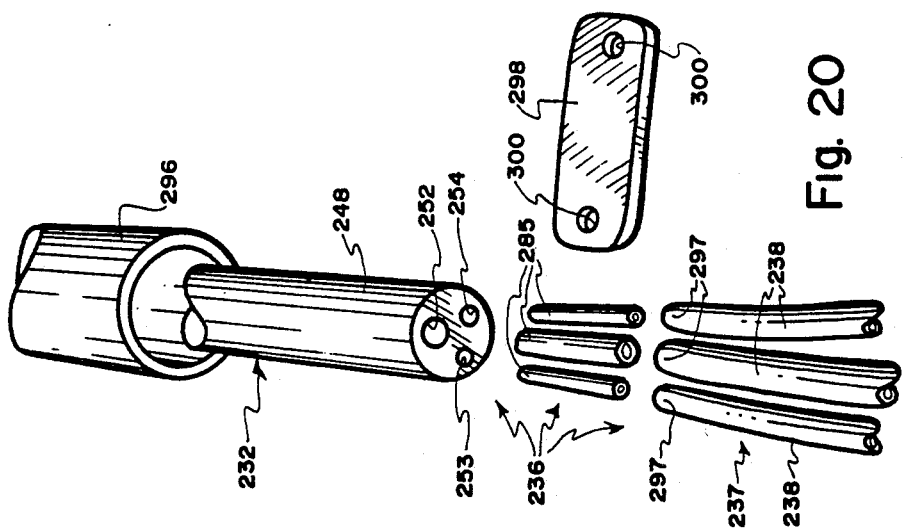
Fig. 20
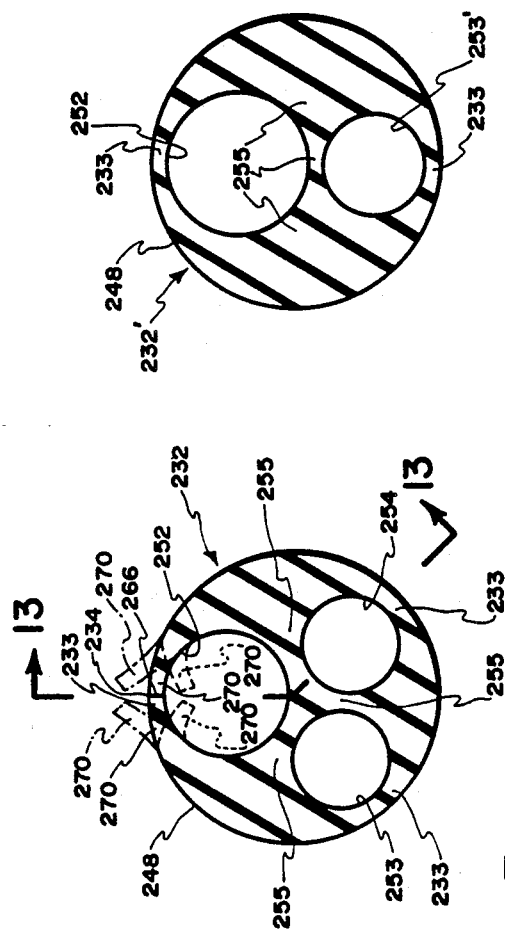
Fig. 12
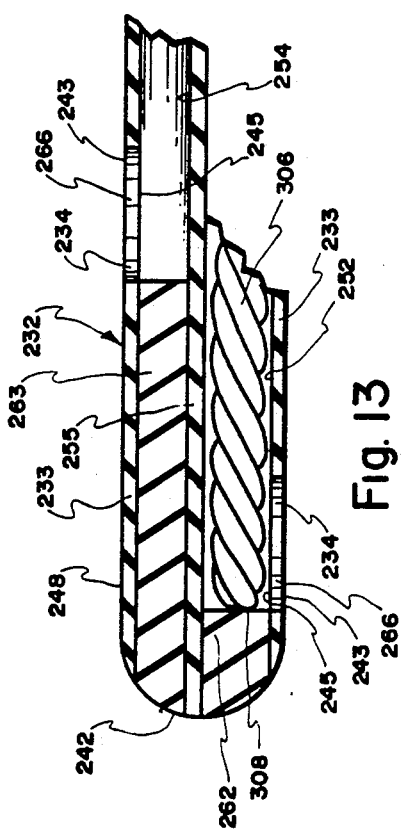
Fig. 13
Fig. 11

CATHETER WITH SLIT VALVE

CONTINUITY

This application is a continuation of our U.S. patent application Ser. No. 915,474, filed Oct. 6, 1986, now U.S. Letters Pat. No. 4,753,640 issued Jun. 28, 1988.

FIELD OF THE INVENTION

The present invention relates generally to catheter slit valves and catheters, catheters having slit valves and, more particularly, novel catheters, catheter slit valve having extraordinary reliability and to multi-lumen catheter assemblies, and related methods.

PRIOR ART

Prior to U.S. Pat. No. 4,327,722 those who proposed placement of a slit valve in the wall of a catheter did so on the basis of the valve being continuously open or where operation thereof is dependent upon unacceptably large pressure variations to open the valve. Chemically weakened slit valves provide high reliability.

It has become state of the art to extrude catheter tubing in cylindrical form where the catheter tubing has one or more lumens which are circular in transverse cross section. When this tubing is kinked, inadvertently or otherwise, the lumen or lumens are fully occluded and flow of liquid therethrough is prevented.

U.S. Pat. No. 4,327,722, entitled Method for Intravenous Therapy and Hyperalimentation, and like prior art discloses a single lumen flexible silicone rubber catheter which has one slit valve adjacent its closed distal end. However, heretofore the use of distal end valves to normally close each lumen of a multi-lumen catheter has been rejected, especially for silicone rubber multi-lumen catheters. See Reissue 31,873 [U.S. Pat. No. 4,072,146]. Reissue 31,873 shows the mentioned state of the multi-lumen catheter art, i.e. use of an external sheath in which a random array of independent lumen-defining tubes are placed wherein the distal tip of each lumen-defining tube comprises an open port in an external sheath. Until the present invention, the superimposing of a valve at the interfacing site between each lumen-defining tube of a multi-lumen catheter and an external sheath thereof was thought impossible.

Alternatively, a single lumen has been used at the distal end of a catheter, with the single lumen being joined to multi-lumens disposed away from the distal end of the catheter. This approach, however, undesirably co-mingles liquids within the single distal end lumen, and does not allow independent use, perhaps simultaneous independent use, of each of several lumens.

The term "distal end", as used herein, refers to the forward end of the catheter which is inserted into the patient's body. The term "proximal end", as used herein, refers to the rearward end thereof which remains outside the patient's body.

BRIEF SUMMARY AND OBJECTS OF THE INVENTION

In brief summary, the present invention comprises catheter tubes of elastomeric material having novel lumen shapes which prevent occlusion and accommodate continued liquid flow even when inadvertently kinked during use.

Furthermore, in abbreviated summary as well, the present invention comprises catheter tube slit valves, the walls of which are mechanically weakened and which provide greater reliability, while avoiding the need for large pressure variations during use. Symmetrical and asymmetrical versions of said slit valve are provided.

Also, novel combinations of highly reliable slit valves and catheter tubes are provided by the present invention.

The present invention also comprises sheathed independently operable multi-lumen catheter assemblies of elastomeric material, including ultra soft elastomeric material such as silicone rubber or polyurethane, wherein each lumen is independently operable and the distal end of at least one lumen is normally closed by a three-position slit valve disposed in an external covering or sheath laterally to one side of the lumen. The plurality of valve sites in the distal end portion of the external covering are disposed in spaced off-set relation. Each slit valve in the external covering normally closes the distal end of one lumen and comprises one or more two-way living hinges.

In addition, the present invention provides multi-lumen catheters, and related methods, wherein each lumen-defining wall is selectively exposed, but concealed at the proximal and distal ends whereby, following placement of the distal end of the catheter tube in the vein of a patient, the unified proximal end of the tube may be manipulated, sometimes subcutaneously, with the exposed tubes ultimately being severed and each equipped with a connector for selective independent passage of influent and/or effluent liquid along each lumen.

With the foregoing in mind, it is an object of great significance to provide elastomeric catheter tubes having novel lumen shapes.

A further paramount object is the provision of a catheter tube having one or more lumens which are uniquely shaped so that occlusion of flow is prevented even when the catheter tube is inadvertently kinked.

An additional object of importance is the provision of novel highly reliable catheter tube slit valves, which hingedly open and close without the need for chemically weakening of the material at the slit valve.

Another dominant object is the provision of extraordinarily reliable slit valves in catheter tubes which avoid any need for large pressure variations during use.

A further significant object is the provision of novel highly reliable mechanically hinged catheter tube slit valves.

A further predominant object is the provision of novel highly reliable symetrical and asymmetrical slit valves.

An object of primary importance is the provision of novel catheter tubes and slit valve combinations.

It is a further primary object of the present invention to provide novel multi-lumen catheter assemblies, and related methods.

Another primary object of the present invention is the provision of sheathed multi-lumen catheters assemblies.

A further important object of significance is provision of multi-lumen sheathed catheters wherein the distal end of each lumen is normally closed by a three-position slit valve.

A further object of consequence is the provision of a multi-lumen catheter of synthetic resinous material wherein a three-position slit valve is disposed in an external covering at the leading end of each lumen.

An additional paramount object of the present invention is the provision of a multi-lumen catheter of synthetic resinous material wherein the leading end of each lumen is closed by a three-position slit valve formed in an external covering, each slit valve comprising at least one two-way living hinge which is either eccentrically or symmetrically disposed.

A further predominant object of the present invention is the provision of multi-lumen catheters, and related methods, wherein each lumen-defining tube is selectively exposed and concealed whereby a single external proximal end and a single external distal end are provided for placement purposes, following which the exposed walls forming the lumens can be severed and each receive a connector for independent use of each lumen.

These and other objects and features of the present invention will become apparent from the detailed description taken with reference to the accompanying drawings.

BRIEF DESCRIPTION OF THE DRAWINGS

FIGS. 1–8 are transverse cross sectional views of catheter tubes embodying the principles of the present invention, each having one or more novel lumen shapes which prevent occlusion and accommodate continued liquid flow even when inadvertently kinked;

FIG. 11 is an enlarged transverse sectional view taken along the lines 2—2 of FIG. 1, showing a larger primary and two smaller secondary lumens;

FIG. 12 is a cross sectional view of a similar catheter showing one larger primary lumen and one smaller secondary lumen only;

FIG. 13 is an inverted enlarged longitudinal fragmentary sectional view taken along the lines 4—4 of FIG. 2, showing the distal end portion of the catheter including two three-position slit valves, and also showing a removable insertion stylet abutting the closed distal tip of the catheter;

FIG. 14 is an enlarged fragmentary exploded elevation of the proximal end of one lumen-defining tube of the catheter of FIG. 1 with the stylet partially removed;

FIG. 15 is an enlarged longitudinally-directed fragmentary cross section of the distal end portion of another multi-lumen catheter embodying the principles of the present invention;

FIGS. 18 and 19 diagrammatically and fragmentarily illustrate the installation of a connector in the form of a hub to the severed end of each lumen-defining tube; and FIGS. 20 and 21 illustrate in exploded fragmentary perspective and fragmentary cross section, respectively, the construction of the connector of FIG. 1.

DETAILED DESCRIPTION OF THE ILLUSTRATED EMBODIMENTS

Reference is now made to the drawings, which illustrate several preferred embodiments of the present invention. Like numerals are used throughout the drawings to reference like parts.

Figure 1:
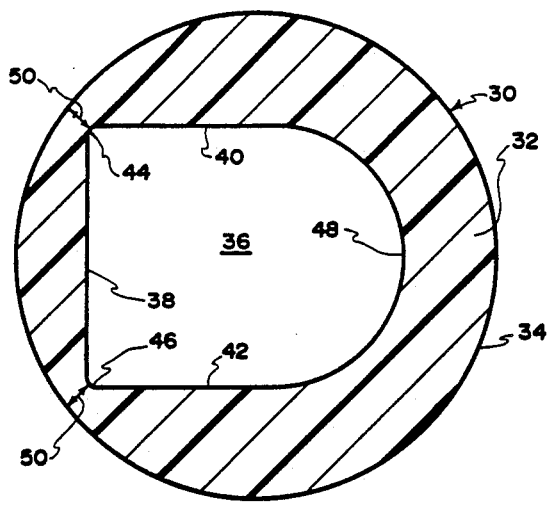

Specific reference is made to FIGS. 1–8, which illustrate in transverse cross section several catheter tubes embodying the principles of the present invention, each having one or more novel lumen shapes which prevent occlusion and accommodate continued liquid flow, even when inadvertently kinked, bent, twisted or collapsed. FIG. 1 comprises a generally cylindrical catheter tube 30, formed of a body of elastomeric material 32 defining an outside smooth cylindrical surface 34 and a single D-shaped axial lumen 36. The lumen 36 comprises linear wall surfaces 38, 40 and 42. Linear wall surfaces 38 and 40 are joined tangentially by a small diameter fillet corner 44 and surfaces 38 and 42 tangentially by a small diameter fillet corner 46. Linear wall surfaces 40 and 42 are joined tangentially by an arcuate wall surface 48.

The location and shape of the corners 44 and 46 define a relatively thin dimension 50 through the body 32, which makes the D-shaped lumen 36 amenable to utilization of certain slit valves fashioned in accordance with the principles of the present invention, as hereinafter more fully described. Furthermore, the nature and shape of the lumen 36 has shown through experimentation to prevent occlusion of the lumen 36 of the catheter tube 30 when the same is kinked, bent, twisted or collapsed. To the contrary, catheter tubing according to the prior art, which utilizes the cylindrical exterior surface and one or more cylindrical internal hollow lumens will result in total occlusion of the lumen or lumens when such prior art catheter tubing is, for example, kinked upon itself through essentially 180 degrees.

Figure 2:
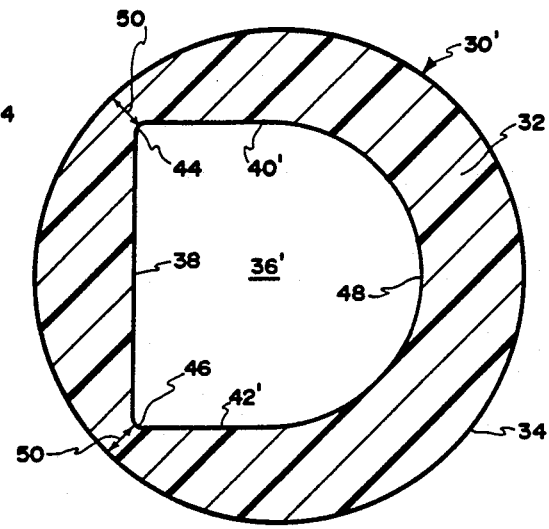
Figure 3:
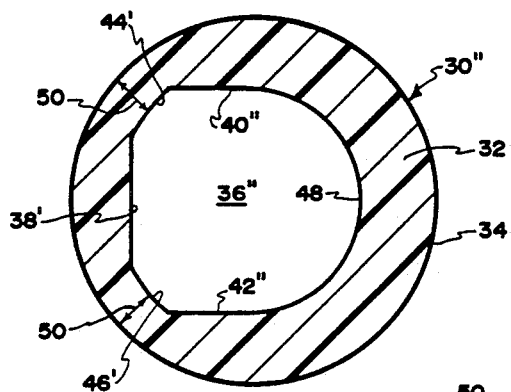

The embodiment of FIG. 2, generally designated 30', is substantially identical in all respects to the catheter tubing 30 of FIG. 1, except that the surfaces 40' and 42' are somewhat shorter in their transverse dimension than previously described wall surfaces 40 and 42. The non-occluding characteristic of catheter tubing 30 also exists when catheter tubing 30' is used.

Likewise, catheter tubing 30" (FIG. 3) is substantially similar to previously described catheter tubing 30 and 30', identical numerals being used to identify substantially identical parts. Catheter tubing 30" differs from catheter tubing 30 in that the flat wall surfaces 40" and 42" are of a substantially smaller width than wall surfaces 40 and 42. Furthermore, the fillet corners 44' and 46' are substantially larger in radius and arc distance than corners 44 and 46 and do not respectively join the adjacent wall surface tangentially. Accordingly, lumen 36" is somewhat smaller than lumen 36 with modified corner structure at each end of the reduced size flat wall surface 38'.

Figure 4:
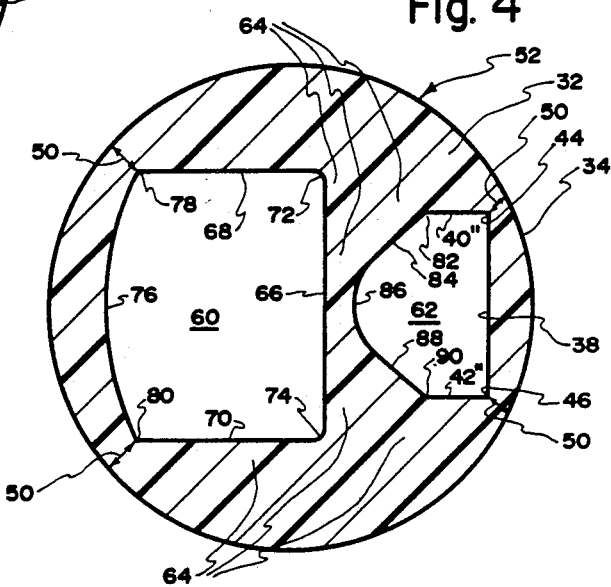

Reference is now made to FIGS. 4–6, which illustrate, respectively, double-lumen catheter tubes 52, 54 and 56. To the extent that catheter tubes 52, 54 and/or 56 have physical parts corresponding to heretofore described catheter tubes 30, 30' or 30", identical numerals are used on FIGS. 4–6 and no further description of those physical parts is deemed necessary to an understanding of the present invention.

Catheter tube 52 comprises primary lumen 60 and secondary lumen 62, each of which define a relatively short distance 50 between an angular lumen corner and the external surface 34 of the catheter tube. The catheter tube 52 comprises an internal body of material 64 which defines and separates the two lumens 60 and 62. Lumen 60 comprises a centrally disposed flat wall surface 66 interposed between two other flat wall surfaces 68 and 70. Wall surface 66 joins wall surface 68 tangentially via corner 72 and wall surface 70 via corner 74. Wall surface 68 and 70 are non-tangentially joined directly one to another by an arcuate wall surface 76, which merges tangentially with the wall surfaces 68 and 70 at fillet corners 78 and 80, respectively.

Catheter tube 52 further comprises a secondary lumen 62, as mentioned above, lumen 62 comprising heretofore described wall surface 38 and fillet corners 44 and 46 tangentially joining relatively small flat wall surfaces 40" and 42" to surface 38. Wall surface 40" is joined angularly or non-tangentially at site 82 to a linear wall surface 84, which tangentially merges with an arcuate wall surface 86. Wall surface 42" likewise joins a flat upwardly angularly directed wall portion 88 at fillet corner 90. Wall portion 88 merges tangentially with arcuate wall portion 86. Thus, catheter tube 52 provides two aligned lumens which provide the relatively short corner spaces 50 to accommodate utilization of highly reliable slit valves as hereinafter more fully explained and which, when the catheter tube 52 is kinked upon itself, will still accommodate liquid flow, as mentioned above.

Double lumen catheter tube 54 is illustrated in FIG. 5. Tube 54 provides internal body and wall structure 64 which provides for separate definition of the two spaced lumens 36'. These lumens, while being somewhat different in size, are substantially identically shaped and each corresponds substantially to the lumen 36' of FIG. 2 already described.

Catheter tube 56 (FIG. 6) comprises a primary D-shaped lumen 92 and a secondary D-shaped lumen 62. Lumen 92 is substantially identical to previously described lumen 36", except the rounded corners 44' and 46' are replaced by diagonally disposed non-tangential wall surfaces 94 and 96, respectively. Diagonal wall surface 94 joins wall surface 40"at angular corner 98 and surface 38' at angular corner 100. Likewise, diagonal wall surface 96 joins wall surface 42" at angular corner 102 and wall surface 38' at angular corner 104. Lumen 62 was heretofore described in connection with catheter tube 52. See FIG. 4.

The non-occluding catheter tubes according to the present invention may comprise more than two lumens defined within the catheter. For example, FIGS. 7 and 8, to which reference is now made, illustrate catheter tubes, according to the present invention, which comprise three lumens, respectively. The catheter tube of FIG. 7 is generally designated 106 and the tri-lumen catheter of FIG. 8 is designated generally as 108.

Catheter tube 106 comprises one primary and two secondary lumens 36". Catheter tube 38' was described earlier in conjunction with in FIG. 2. Accordingly, no further description is deemed necessary in respect to the lumens of catheter tube 106, except to say that the lumens are illustrated as being disposed, respectively, along predetermined radial lines, consistent with the requirements of structural integrity needed for indwelling catheters and so as to provide corner sites 50.

Likewise catheter tube 108 comprises one primary and two secondary lumens 62, previously described in conjunction with catheter 56, shown in FIG. 6. No further description is, therefore, deemed necessary, it being understood that the lumens 62 of catheter tube 108 are illustrated as being arranged along predetermined radial lines so that the corners 44 and 46 thereof create corner sites at locations 50.

It is presently believed that the relatively thin regions 50 coupled with the adjacent lumen corner structure accounts for the aforementioned non-occluding feature of catheter tubes according to the present invention.

Not only do the novel lumen shapes for catheter tubes according to the present invention prevent occlusion of the lumens where the catheter tube is kinked, flattened, or the like, the novel lumens have been found to aid materially in the provision of novel slit valves according to the invention.

Figure 9:
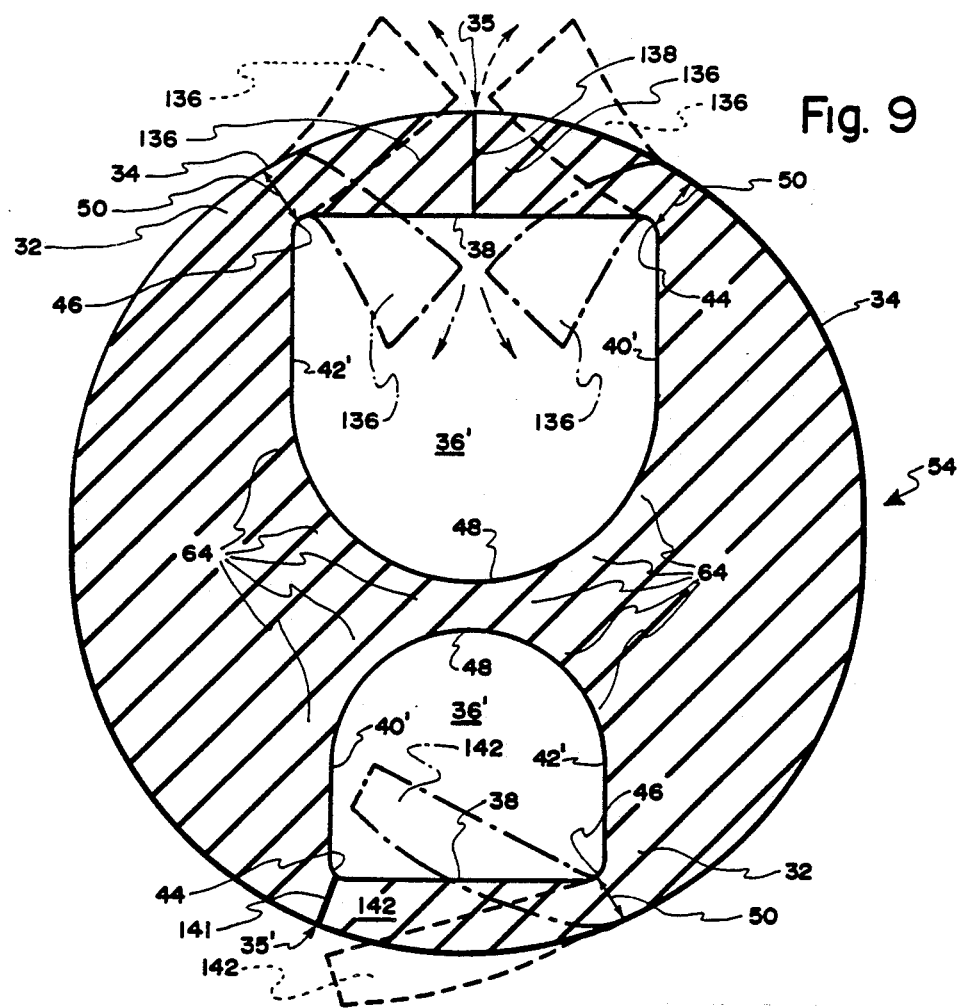
FIG. 9 is an enlarged transverse cross section of the distal end of another two-lumen catheter embodying the principles of the present invention.

Two such hinge action slit valves 35 and 35' are illustrated in FIG. 9.

FIG. 9 shows the distal end portion of two-lumen catheter 54, described earlier in conjunction with FIG. 5 and having D-shaped primary and secondary lumens 36'. The distal end portion of tube 54 comprises exterior covering 32 and internal wall structure 64, which defines the lumens 36. Corners 44 and 46 of the lumens 36' are located closer to the exterior covering surface 34 than any other part of the lumens 36'. Thus, corners 44 and 46, in each case define two hinge or fold lines or regions 50 where the catheter wall is thinnest. Relatively thicker areas 136 are disposed between hinge sites 50. The slit 138 of slit equidistant between the hinge sites 50 of the primary lumen 36'.

The D-shaped lumens 36' are structurally stronger than conventional round catheter tube lumens. Therefore, lumens according to the present invention are more resistant to collapse under high negative pressures. The D-shaped lumens also offer two principal advantages in the operation of the valve 35. First, the thicker walls adjacent the self sealing slit 138 create a larger sealing surface area for the valve lips 136, and, therefore, create a more positive seal when the distal end portion of tube 54 is indwelling and under normal physiological pressures. Second, the flex of the valve 35 is concentrated at the hinge sites 50, which sites are located some distance from the slit 138. This concentration of the flex in a relatively small hinge site provides for more consistent operation, more reliable response to predetermined pressure differentials designed to open and close the valve, a wider valve opening, and a longer life of the valve 35. The use of thickened valve lips 136 also serves to raise the withdrawal threshold, providing for a more positive, highly reliable valve action.

FIG. 9 also diagrammatically illustrates an eccentric slit valve 35' comprising a single slit 141 disposed in one corner 46 of the secondary lumen 36'. In this configuration, the hinge action is concentrated at the single hinge site 141, illustrated as intersecting the other lumen corner 44. Thus, the entire asymmetrical valve lip 142 is hingedly displaced, inwardly or outwardly, to create the valve orifice. This eccentric configuration accommodates, with high reliability, use of the slit valve 141 in catheters having lumen sized too small to provide consistent operation of a symmetrical slit valve. The two slit valves illustrated in FIG. 9 are shown, for ease of illustration, as being in the same transverse plane. However, in actual fabrication the slit valves are preferably longitudinally and radially offset each from the others. In limited testing to date, the eccentric valve 35' has proved better in use than concentric valve 35, where the catheter lumen size was relatively small.

Figure 10:
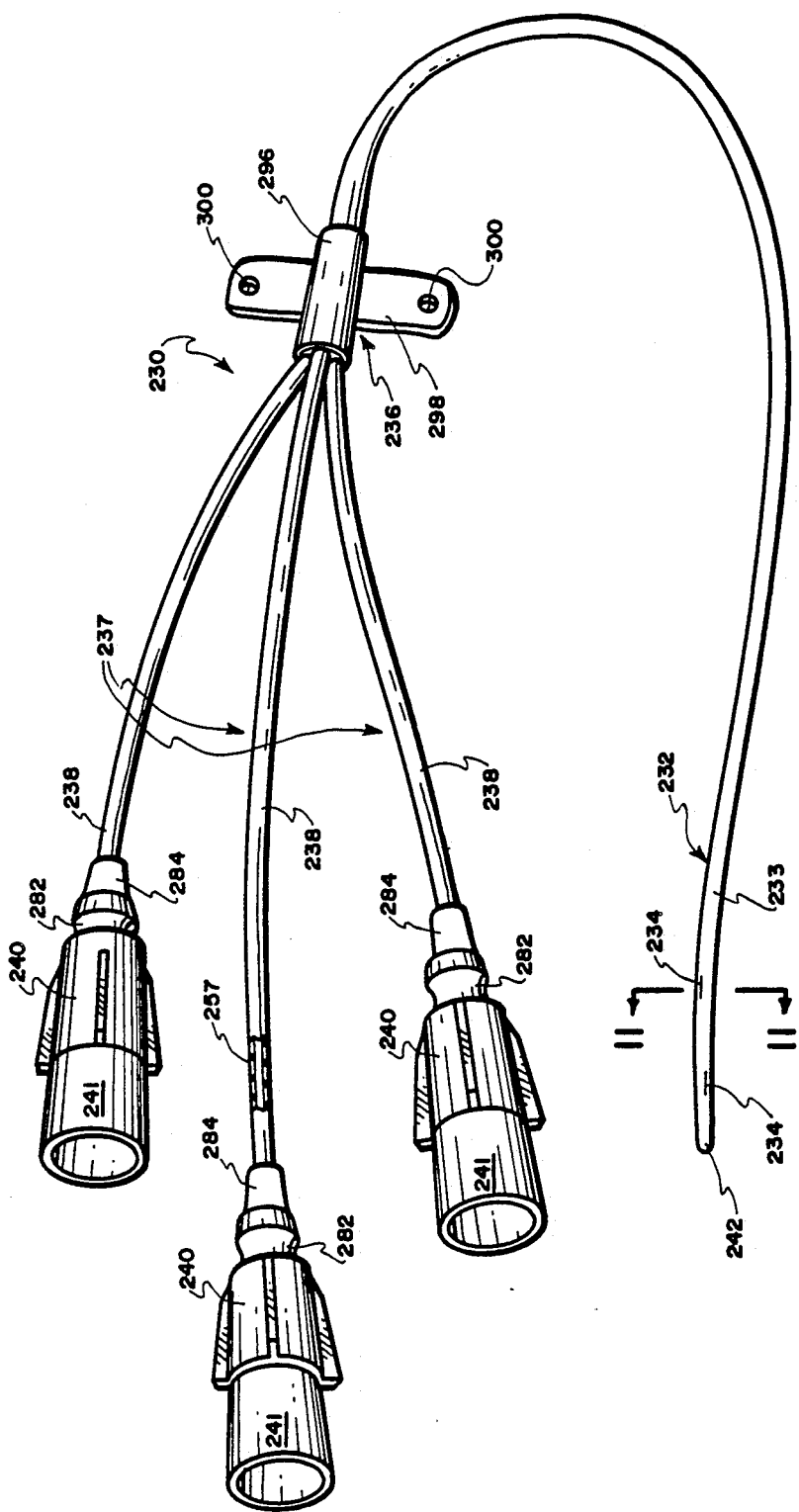
FIG. 10 is a perspective representation of a three-lumen catheter fabricated in accordance with the principles of the present invention.
Figure 17:
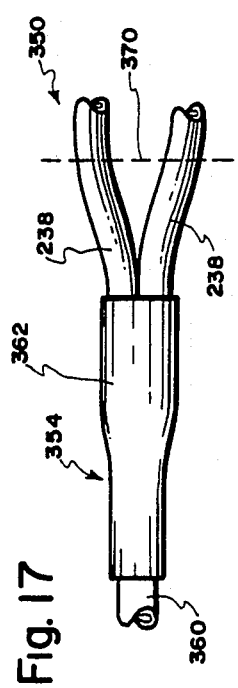
FIG. 17 diagrammatically and fragmentarily illustrates sites where the exposed lumen-defining tubes of the catheter of FIG. 9 are severed during placement of the catheter preparatory for use.

It is to be understood that the present invention embraces the aforedescribed slit valves comprising one or more mechanically weakened hinge regions independent of whether the wall regions of the slit valves are or are not chemically treated. Specific reference is made at this time to FIGS. 10-14 which illustrate a further presently preferred catheter, generally designated 230, fabricated according to the principles of the present invention. FIG. 10 shows the catheter 230 to comprise several major parts: i.e. (1) a distal end portion 232, adapted for insertion into a vein or other body cavity of a medical patient and comprising an exposed external sheath or covering 233 and internal wall structure 255, which defines a plurality of independent and separately operable circular lumens for carrying liquids to or from a desired body cavity; 2) a three-position pressure activated slit valve 234 forming a normally closed lateral gate or port shown as being disposed at the distal end of each catheter lumen, each slit valve 234 being controlled by the application of positive or negative pressures to the associated lumen of the catheter 230; (3) a coupling or transitional member 236 connecting the distal end portion 232 to a proximal end portion 237 which comprises a number of lumen-defining tubes 238; (4) the proximal end portion 237 of the catheter 230 comprising tubes 238 which respectively extend the lumens of the catheter to exposed hubs 240, of a conventional type, which accommodate connection to various fluid infusion and withdrawal and like devices; and (5) terminal hubs 240, each shown as being closed by a conventional plug 241.

Each three-way valve 234 normally prevents flow but provides for selective positive control of the liquid flow only through the associated lumen. By applying a predetermined positive pressure to the lumen terminal hub 240, with the stopper 241 removed, a desired liquid is infused into the vein of a patient by forcing the associated valve 234 to hingedly open. By applying a negative pressure, liquid within a body cavity is withdrawn. Under normal physiological pressures, the valve 234 will remain closed and sealed.

The distal end portion 232 is typically cylindrical in shape, as shown in FIG. 2. However, the exterior surface may take other forms. The distal end portion 232 is preferably slender in diameter, allowing the closed distal tip 242 to be facilely introduced into a vein or other cavity and advanced to a desired treatment location, while the proximal end 237 remains outside the body. The length of the distal end portion 232 will, therefore, vary with its intended application. The distal end portion 232 is illustrated as having a uniform though relatively small exterior diameter so that it can be readily inserted into a vessel, such as the subclavian vein, without causing undue trauma to the patient. Typically, this requires that the distal end portion 232 have an outside diameter not exceeding about 0.125 inches (0.318 cm). The distal tip 242 of the distal end portion 32 is preferably dome-shaped and smoothed to further minimize trauma.

As shown in FIG. 13 (in inverted and angular sectional view with respect to FIG. 11), the array of slit valves 234 is formed in the sheath 233 and exposed at the exterior cylindrical surface 248 thereof, at site 243. Each valve 234 is also exposed laterally to one of the lumens, at sites 245. The valve sites are radially distributed in offset relation around the distal end portion 232 near the tip 242 so that no two valves 234 lie in any one radial plane. The valves 234 are also longitudinally separated or offset in their placement at relatively short but different distances from the distal tip 242 so that no two valves 234 lie in any one axial plane. The radial and longitudinal separation of the valves 234 helps avoid structural weakness and helps prevent possible contamination of an influent sample withdrawn from one valve 234 by an infusion stream of effluent liquid from another valve 234 passing into the vein of a patient, which might adversely affect test results or result in premature mixing of incompatible therapeutic liquids. It should be noted that longitudinal separation should not be used where the effect would be to position any valve 234 out of the desired treatment or exposure area.

The distal end portion 232 is made of a durable and pliable yet shape-retaining biocompatible synthetic elastomeric material. It is presently preferred that the material comprise an ultra soft synthetic material. Typically, such material should have a hardness of less than 100 durometer and an elongation percentage of up to 700. A preferred material is a silicone rubber tubing having a hardness of about 59 durometer sold under the trade name SILASTIC by Dow Corning Co., Midland, Mich. The distal end portion 232 is preferably at least partially radiopaque so that its precise position in the body may be radiologically verified. Tubes 237 are preferably transparent so that the physician can visually determine the presence of air bubbles, blood, or other liquids in each of the lumens during and after insertion.

As illustrated in FIG. 11, three independent lumens 252, 253 and 254 are longitudinally disposed inside the distal end external covering 233, the lumens typically being radially distributed at predetermined angles beneath the exterior cylindrical surface 248 of the distal end portion 232 in such a way that an interior lumen wall surface passes within a relatively short distance of the exterior surface 248 of the exterior covering 233, as measured along a radial line passing through the center of each lumen 252, 253 and 254. It is apparent from the radial disposition of the lumens in close proximity to the exterior surface 248 that valves 234 installed along a radial line in the fashion just described or installed in any consistent position relative to the lumens 252, 253 and 254 will necessarily be radially separated from each other as previously discussed. Interior walls 255 (FIG. 11) respectively form and define the size and shape of the lumens 252, 253 and 254 at the distal end portion 232. Tubular, hollow walls 257 respectively form and define the size and shape of lumens 252, 253 and 254 at the proximal end portion 237.

Note from FIG. 12 that a double lumen catheter having a proximal end portion 232' is also within the scope of the present invention. Proximal end portion 232' comprises primary lumen 252 and secondary lumen 253'.

Each lumen 252, 253 and 254 extends from the associated hub 240 at the proximal end portion 237 to a point near the distal tip 242. See FIG. 10. The larger or primary lumen 252 extends substantially the entire length of the catheter 230, terminating in a closed tip wall portion 262 adjacent the distal tip 242 of the distal end portion 232. See FIG. 13. Secondary lumens 253 and 254 terminate in similar closed end wall portions 263, only one of which is illustrated in FIG. 13. The lumens terminate at relatively short but different distances from the distal tip 242, for the purpose of providing longitudinal separation of the valves 234, as previously described.

In the embodiment of FIGS. 10, 11, and 13, the proximal end portion 232 is preferably formed by extrusion, for reasons of simplicity and ease of construction, but other methods may be used. When extruded, the lumens 252, 253 and 254 and the interior walls 255 forming the lumens 252, 253 and 254 are continously formed during extrusion; thus, each lumen is of a uniform cross-sectional shape, being cylindrical or circular in the embodiment of FIGS. 10, 11 and 13.

In the extruded embodiment of FIGS. 10, 11 and 13, the closed end wall portions or plugs 262 and 263 are formed by injecting a suitable silicone rubber adhesive or the like into the leading ends of lumens 252, 253 and 254 for the distance from the distal tip 242. The adhesive then hardens to form the closed end wall portions or plugs 262 and 263, each up to the leading edge of the associated valve 234. If a radiopaque distal tip 242 is desired, this may be accomplished by mixing a radiopaque material with the adhesive prior to injection to form plugs 262 and 263.

One three-position valve 234 is placed in the covering adjacent to and laterally interfacing with each lumen 252, 253 and 254 adjacent the plug 262 or 263. Each valve 234 is formed by a single relatively short slit 266 in the covering 233. Each slit extends longitudinally along the exterior of covering 233 parallel to but offset from the axis of the distal end portion 232. The thickness of each slit valve 234 is equal to the thickness of covering 233, so as to provide for selective liquid communication between the interior of the lumen 252, 253 and 254 with the exterior of the distal end portion 232. Each slit valve 234 is illustrated as being radially directed and symmetrically disposed in its corresponding lumen 252, 253 and 254 at the thinnest point in the covering 233. Thus, each slit valve 234 comprises two valve lips or walls 270 which comprise blunt edges. These edges contiguously mate and seal along the slit 266 under normal indwelling pressure conditions.

FIG. 11 shows the operation of each three-position slit valve 234. Upon application of a predetermined pressure differential between the interior and exterior of the distal end portion 232, the valve wall will hingedly deflect or flex causing the valve lips 270 to separate at slit 266, creating a flow path-defining orifice through which liquid may pass in or out of the selected catheter lumen 252, 253, 254, when the distal end portion 232 is indwelling. When the indwelling pressure inside the selected catheter lumen 252, 253, 254 exceeds the indwelling pressure outside the distal end of the catheter by a predetermined amount (the "infusion threshold"), the valve immediately surrounding the slit 266 deforms, and the lips 270 of the valve 234 are caused to separate hingedly in an outward direction thereby creating an orifice through which liquid is infused into the blood stream, as shown in FIG. 11. Likewise, the application of a sufficient degree of negative pressure (the "withdrawal threshold") to the selected catheter lumen 252, 253, 254 will cause the valve lips 270 to flex hingedly inwardly, also as shown in FIG. 11, allowing withdrawal of blood or other fluids from the bloodstream or other body cavities.

Under normal physiologic conditions, as stated above, each slit valve 234 remains closed and sealed, as shown in solid lines in FIG. 11. This requires that the catheter tube have sufficient memory to return to the closed sealed edge-to-edge position when liquid flow conditions terminate. When used in the cardiovascular system, the withdrawal threshold must also be high enough to prevent back bleeding under normal systolic pressures in the circulatory system of a patient. The infusion threshold must likewise be high enough to overcome the normal venturi effect of blood flowing past the indwelling valve 234. The infusion and withdrawal thresholds should not be so high as to make infusion or withdrawal difficult.

Both the infusion and the withdrawal thresholds can be adjusted either by controlling the thickness and configuration of the valve walls or lips 270 or by selectively treating the valve walls with a biocompatible softening agent such as dimethylsiloxane, as is more completely disclosed in U.S. patent application Ser. No. 491,258, filed May 3, 1983, now U.S. Pat. No. 4,549,879. It should also be noted that the valve 234 may, if desired, be treated with an anticoagulant, such as Heparin. However, the design of the catheter 230 disclosed herein does not require such treatment.

The liquid flow capacity of the lumens may vary with the intended application of the catheter 230. The lumens must, of course, be large enough to accommodate the desired fluid flow, while the thickness of the walls forming the lumens must be adequate to prevent rupture or inadvertent puncture and consequent leakage either between lumens or to or from the exterior.

The slit valve 234 must be the weakest point in each lumen 252, 253 and 254. Each part of each catheter lumen must be stronger and more rigid than the valve lips 270, since collapse or rupture of any other part of the catheter would defeat the purpose of the catheter 230. It is, therefore, important that the lumen walls be strong enough to stand the full range of lumen pressures without rupture, inward collapse or other failure, which would impair proper operation of the slit valves 234.

While from a practical point of view, the utilization of a single extruded tube comprising multiple lumens for the distal end portion 232 is effective and low-cost, it is to be appreciated that the distal end portion 232 can be otherwise fabricated. For example, with reference to FIG. 15, the distal end 232" may comprise separate spaced lumen-defining tubes 274, 276 disposed within a hollow cavity 278 of an external thin walled cylindrical sheath or covering 233', which has a smooth cylindrical exterior surface 248'. The proximal edges of the tubes 274, 276 are secured by satisfactory adhesive to the interior of the sheath 233'at sites 280. The resulting lumens 252' and 253" respectively transversely interface with a slit valve 234 disposed in the wall of the sheath 233'. No further discussion of the slit valve 234 is deemed to be necessary in light of the prior description thereof. The distal tip 242' of the distal end portion 232" is configured so as to be shaped substantially the same as the heretofore described distal tip 242. The tip 242' does provide an internal circular transverse flat wall 283 against which an insertion stylet or insertion stiffener abuts when placed within the primary lumen 252', in a manner and for purposes hereinafter more fully described.

Returning now to the embodiment of FIGS. 10, 11 and 13 the proximal end portion 237 of the catheter 230 is joined via a connector 236 to a plurality of separate lumen-defining tubes 238. Tubes 238 may be made of an ultra-soft synthetic material or other elastomer, similar to the material of the distal end portion 232, previously described. However, the tubes 238 must be strong enough to resist collapse or rupture and the additional environmental hazards of an exposed tube. Each tube 238 may, therefore, be strengthened by using a tubing with thicker walls and/or a higher durometer. Tubes 238 are preferably at least partially transparent or translucent to accommodate visual monitoring of the contents therein. Unlike distal end portion 232, however, the proximal tubes 238 have no need for radiopacity, because they are not intended to be indwelling.

Tubes 238 are most economically constructed of a tubing with concentric inner and outer cylindrical wall surfaces, thereby forming walls of uniform thickness providing a predetermined inside diameter equal to that of lumens 252, 253 and 254 of distal end portion 232. The outside diameter of connector tubes 238 should be large enough provide a wall thickness at 257 adequate to resist abrasion and puncture. The trailing edge of each tube 238 is preferably perpendicular to the axis thereof. This accommodates connection of hub 240 at short hollow shaft 282 thereof, using a sleeve coupling 284. See FIGS. 11 and 14. Each sleeve coupling may be secured in the stated and illustrated position using conventional material-shrinking techniques.

The connector 236 is constructed by permanently connecting each lumen 252, 253 and 254 to one of the tubes 238 by use of a hollow coupling tube 285. See FIG. 20. Each coupling tube 285 may be made of surgical steel, although other materials can be used. Preferably each coupling tube 285 has an inside diameter substantially the same as the inside diameter of the catheter lumen 252, 253, 254, to which it is attached so as to minimize if not prevent any flow restriction at the connector 236. The outside diameter of each coupling tube 285 should, therefore, be slightly larger than the inside diameters of lumens 252, 253, 254 and tubes 238. Thus, each tube 285 is force fit into lumens 252, 253, 254 at the body of connector 236, expanding each at the insertion sites. The leading end 297 of each tube 238 is force fit over the trailing end of the associated connector tube 285. See FIG. 21.

The entire joint or connector 236 is preferably secured with silicone rubber adhesive 264 or other appropriate sealant, and finally shrink-wrapped by soaking a tubular silicone rubber sleeve 296 in Freon or other solvent material causing it to temporarily expand, and slipping the sheath 296 over the connector 236. As the solvent evaporates the sheath 296 permanently contracts firmly around the remainder of the connector 236, adhering to the adhesive 264 and forming a secure and protected joint.

Suture wing 298 is illustrated as being attached to the connector 236 so that the catheter 230 at connector 236 may be sutured in place after the distal end thereof is indwelling. The suture wing 298, shown in FIGS. 10, 20 and 21 is fashioned from a small piece of silicone rubber sheet cut in the illustrated elongated shape and having circular holes 300 disposed in the ends thereof to receive sutures. Suture wing 298 may also help to prevent the catheter 230 from rolling or shifting when taped in place on a patient as opposed to suturing in place. The suture wing 298 is preferably attached to the connector 236 using silicone rubber adhesive or another suitable method.

When the catheter tube 232 is formed of soft, pliable material, a stylet or inserter 306 is preferably used to rigidify the distal end portion 232 during insertion. In the illustrated embodiment, stylet 306 is illustrated as being formed of twisted surgical grade wire. The stylet 306 is illustrated as being equipped with an integral proximal hub 307, by which the stylet is manipulated. See especially FIGS. 13 and 14. It could also be formed of any yieldable and shape retaining biologically inert material such as polypropylene. Stylet 306 is preferably inserted into the primary lumen 252, until its distal tip 308 abuts the closed wall 262. During insertion, a force manually applied to the stylet 306 causes the distal end thereof 308 to push against closed end 262 of the primary lumen 252. This places the covering 233 under tension, causing the distal end portion 232 to be pulled forward into the vein of the patient, for example.

Primary lumen 252 must naturally be dimensioned large enough to accommodate the stylet 306. The walls 255 defining the primary lumen 252 and the covering 233 should also be thick enough to prevent accidental penetration by the stylet 306, which could result in undesired communication between lumens or trauma to the patient.

The stylet tip 308 should also be constructed to prevent penetrating the primary lumen 252 through the slit valve 234 or through the tip or head 242. In this regard, the abuttment 262 of primary lumen 252 may be formed a sufficient distance from the slit valve 234 to allow an adequate safety margin against stylet damage at the valve site 234.

The distal tip 308 of stylet 306 is kept in constant pressure contact with the abuttment 262 of primary lumen 252, during storage and insertion, as shown in FIG. 13. The stylet 306 is of slightly longer overall length than the primary lumen 252, so that the distal tip 308 of stylet 306 not only abuts the distal closed end 262 of the primary lumen 252, but the stylet hub 307 is exposed beyond the terminal hub 240 in the fully assembled condition. When the stylet hub 307 is seated as a closure in the terminal hub 240, a tension is created in the distal end portion 232 and the remainder of the catheter 230 by the forced engagement of the distal tip 308 of the stylet 306 against the distal closed end 262 of the primary lumen 252.

It will be recognized that a central feature of the invention is that the infusion and withdrawal thresholds of each three-position valve 234 may be selected to meet the needs of any particular application. In respect to the embodiment of FIGS. 10-15 and 21, this may be done chemically, as previously described. In the case of the embodiment of FIGS. 1-9, it is accomplished mechanically by providing a weakened hinge or fold line in the covering of the catheter tube. It is also to be noted that while the mechanically hinged valve is of particular importance in multi-lumen catheters, the principles thereof, comprising part of the present invention, also apply to single-lumen catheters.

In FIG. 11, for example, the lumens 252, 253, 254 have a circular cross section. Because of the convex curve of the valve wall 268, the valve lips 270 flex somewhat more easily outwardly than inwardly. As a result, the withdrawal threshold is typically somewhat higher than the infusion threshold. Because the exterior surface 248 of the covering 233 is not concentric with respect to the curvature of the lumens 252, 253, 254, the valve wall lips 270 increase in thickness with distance from either side of the slit 266. As a result, the valve 234 requires higher pressure differentials to open fully than it does to merely break the seal at the slit. By modifying the dimensional relationship between the inside walls 255 defining the interior lumens 252, 253, 254 and the outside sheath surface 248 different valve threshold pressures and operating characteristics may be obtained.

Figure 16:
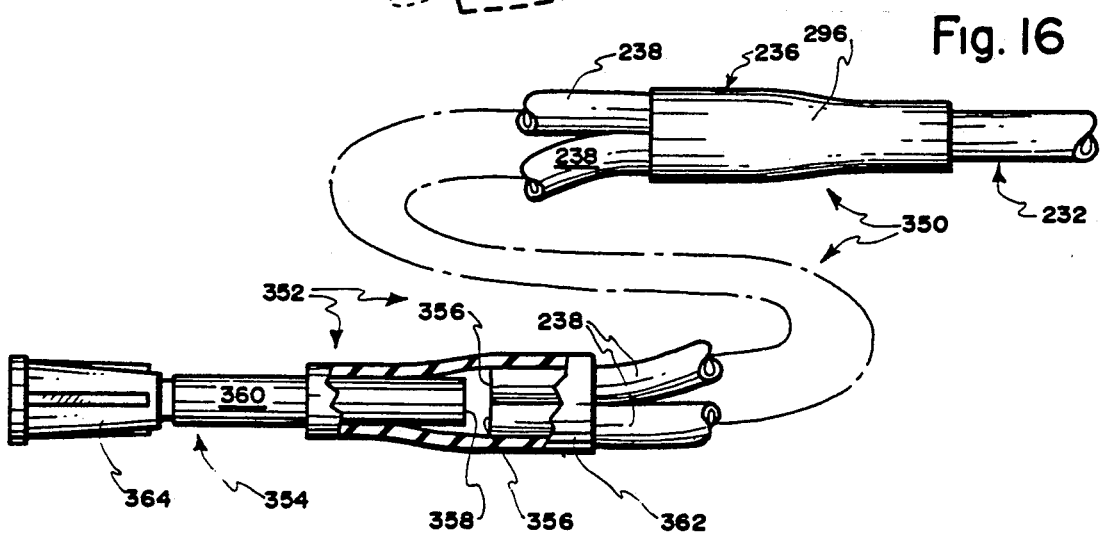
FIG. 16 is a plan view of still another multi-lumen catheter of the present invention, showing two coupling sites one of which is broken away for clarity of illustration.

FIGS. 16-19 illustrate another presently preferred embodiment of the present invention, namely a two-lumen catheter generally designated 350 in FIG. 16, constructed in accordance with the present invention for long term indwelling use with a patient. A trocar (not shown), for example may be used to position most of the proximal end of the catheter 350 subcutaneously as hereinafter explained in greater detail. The construction of the catheter 350 is essentially the same in many respects to the catheter 230. Therefore, only the differences will be described.

The catheter 350 at the proximal end portion 352 thereof comprises two lumen-defining tubes 238. However the tubes 238 do not each terminate in hubs 240 as with catheter 230 of FIG. 1. Rather, the two tubes 238 are collectively joined to a common hub structure 354.

FIG. 11 shows the presently preferred construction of the proximal common hub 354. The tubes 238 are brought together into side-by-side contiguous relation with their blunt trailing ends 356 aligned. The leading blunt end 358 of a single short cannula 360 of hub structure 354 is placed in close proximity to and generally in alignment with the blunt ends 356 of tubes 238. See FIG. 16. A suitable silicone rubber adhesive is extruded over the ends 356 and 358. A cylindrical sleeve 362 is diametrically expanded by soaking it in freon, as previously described, and positioned over the joint so as to shrink into firm contact with the adhesive and thus tightly seal the joint at either end.

The common cannula 360 is fitted at its proximal end with a stylet hub 364 to which a stylet of the type previously disclosed is attached. The use of the stylet hub 364 connected to the common cannula 360 offers the advantage of being able to simultaneously flush all of the lumens comprised in the interior of the tubes 238 of the catheter 350 from a single syringe (not shown) or the like.

Once the distal tip 242 of the catheter 350 is properly placed in a desired indwelling position by surgery or other methods known in the art, the stylet hub 364 and the attached stylet are removed from the proximal end. A trocar (not shown) is conventionally releasably attached to the cannula 360. The trocar and the attached cannula 360 are then passed subcutaneously through the body to a convenient exit site.

Once the catheter 350 is properly placed, typically at a site readily accessible to the patient, the tubes 238 are transversely severed along cut line 370 (FIG. 17) adjacent the coupling sleeve 362. Each severed end 372 of each tube 238 is thereafter fitted with a permanent terminal hub 374 by any suitable method. One such method is essentially disclosed in existing U.S. Pat. No. 4,547,194. The method illustrated in FIGS. 18 and 19 comprises provision of the terminal hubs 374 which respectively comprise a short hollow shaft 376. The outside diameter of the short shaft 376 is illustrated as being substantially the same as the outside diameter of the tube 238. Accordingly, when the short shaft 376 is advanced into the smaller diameter lumen-defining hollow interior of the associated tube 238, as illustrated by lines 370 in FIG. 18, the trailing end of tube 238 is stretched radially causing the inside diameter of the tube 238 to become the same as the outside diameter of the short shaft 376, as illustrated in FIG. 19. The memory of the synthetic resinous material from which each tube 238 is made applies a compressive radial force against the short shaft 376 thereby retaining against inadvertent separation the described union created between each hub 374 and the trailing end of the associated tube 238.

By placing the two trailing ends of the tubes 238 (with hubs 274 in the position of FIG. 19) at a convenient body site accessible to the patient, the patient himself may comfortably utilize the catheter 350. While during periods of non-use, the hubs 374 can be plugged with conventional plugs (not shown), the hubs during use, can be connected, for example, to an artificial kidney machine whereby blood from the subclavian vein, for example, can be removed through one tube 238 for processing through the artificial kidney machine and the effluent from the machine can be returned to the bloodstream through the other tube 238.

The invention may be embodied in other specific forms without departing from the spirit or essential characteristics thereof. The present embodiment is, therefore, considered in all respects as illustrative and not restrictive, the scope of the invention being indicated by the scope of the appended claims rather than by the foregoing description, and all changes which come within the meaning and range of equivalency of the claims are therefore intended to be embraced therein.

What is claimed and desired to be secured by U.S. Letters Patent is:

1. An indwelling multi-lumen catheter comprising:
   a catheter tube made of biocompatible material, the catheter tube comprising a distal end portion having a single smooth exterior surface and ending in a closed distal tip, a proximal end portion, and wall means defining a plurality of independently usable lumens extending substantially the entire length of the catheter tube;
   a normally sealed, selectively operable, laterally disposed, three-position slit valve communicating between the distal end of one of the lumens and the exterior surface of the distal end portion, the slit valve affording selective influent and effluent flow control into and out of the lumen associated therewith;
   the slit valve comprising a slit extending through the wall, the slit being essentially parallel to and offset from the axis of the catheter tube and being defined by opposed, aligned, normally sealed, parallel first and second edges of respective oppositely disposed first and second slit valve wall segments of the wall between the associated lumen and the exterior surface of the distal end portion, the first slit valve wall segment being pivotably displaceable inwardly and outwardly responsive to predetermined liquid pressure differentials between the pressure in the associated lumen and the pressure exterior to the catheter tube, thereby to pivot the first edge into a spaced-apart spatial relationship from the second edge, whereby the first edge is capable of selectively opening either outwardly from the normally sealed position to infuse fluid from the one of the lumens into the space exterior to the distal end portion, or inwardly from the normally sealed position to withdraw fluid from the space exterior to the distal end portion into the one of the lumens, the first slit valve wall segment being eccentrically disposed in the slit valve with the slit being asymmetrically disposed between the two slit valve wall segments in offset relation to the center of the slit valve.

2. An indwelling multi-lumen catheter comprising:
   a catheter tube made of biocompatible material, the catheter tube comprising a distal end portion having a single smooth exterior surface and ending in a closed distal tip, a proximal end portion, and wall means defining a plurality of independently usable lumens extending substantially the entire length of the catheter tube;

a normally sealed, selectively operable, laterally disposed, three-position slit valve communicating between the distal end of one of the lumens and the exterior surface of the distal end portion, the slit valve affording selective influent and effluent flow control into and out of the lumen associated therewith;

the slit valve comprising a slit extending through the wall, the slit being essentially parallel to and offset from the axis of the catheter tube and being defined by opposed, aligned, normally sealed, parallel first and second edges of respectively oppositely disposed first and second slit valve wall segments of the wall between the associated lumen and the exterior surface of the distal end portion, the first slit valve wall segment being pivotably displaceable inwardly and outwardly responsive to predetermined liquid pressure differentials between the pressure in the associated lumen and the pressure exterior to the catheter tube, thereby to pivot the first edge into a spaced-apart spatial relationship from the second edge, whereby the first edge is capable of selectively opening either outwardly from the normally sealed position to infuse fluid from the one of the lumens into the space exterior to the distal end portion, or inwardly from the normally sealed position to withdraw fluid from the space exterior to the distal end portion into the one of the lumens, said slit valve further comprising a first hinge means located at a side of the first slit valve wall segment remote from the slit for concentrating inward and outward pivoted displacement of the first slit valve wall segment.

3. A catheter according to claim 2 further comprising a removable flexible wire-like catheter tube inserting push member initially removably positioned within the interior of one lumen, the distal end of the wire-like member directly abutting the interior of the closed distal tip of the distal end portion of the catheter tube, said wire-like member having sufficient stiffness whereby applying a manual pushing force to said wire-like member will cause the wire-like member to push directly against the closed distal tip of the catheter tube thereby causing the catheter tube to be subjected to a tensile force during insertion of the distal end of the catheter tube into and advance it within the body cavity, the wire-like member having sufficient flexibility to enable it to follow the contours of the body cavity, the proximal end of the wire-like member being accessible at the proximal end of the associated lumen for removal after said insertion of the catheter tube.

4. A catheter according to claim 2 wherein the slit valve comprises two symmetrical slit valve wall segments.

5. An indwelling catheter tube comprising an external surface, a closed distal tip, at least one liquid transmitting internal lumen, a wall layer of material interposed between the lumen and the external surface adjacent the distal end of the lumen, and a normally closed slit valve, said slit valve comprising a slit formed through said wall layer, a valve wall adjacent to the slit, and a hinge disposed between the valve wall and the adjacent wall layer, the hinge comprising a localized region of reduced thickness spaced a predetermined distance from the slit, whereby predetermined indwelling liquid pressure differentials between the pressure in the lumen and the pressure outside the exterior surface will open and close the slit by pivoting of the valve wall at the localized reduced thickness region.

6. An indwelling catheter tube according to claim 5, wherein the lumen has a cross section that is transversely asymmetrical and comprises at least one corner, the corner forming part of the localized reduced thickness region.

7. An indwelling catheter tube according to claim 5, wherein the localized reduced thickness region is also chemically softened.

8. A multi-lumen catheter comprising a catheter tube comprising wall means comprising inside and outside surface means, the inside surface means defining at least two asymmetrically-shaped lumens, an externally exposed slit valve disposed in the wall means normally closing the distal end of each lumen, each slit, valve comprising a slit, valve wall means adjacent the slit and a hinge comprising a region of reduced thickness disposed at the convergence of the valve wall means, the catheter wall means and lumen-defining surface means.

9. A multi-lumen catheter according to claim 8 wherein the hinge of at least one slit valve is disposed at a single localized site and the slit thereof is spaced from the hinge and eccentrically disposed in said slit valve.

10. A multi-lumen catheter according to claim 8 wherein at least one slit valve comprises a region of reduced thickness disposed at two spaced localized hinge sites with the slit thereof symmetrically disposed in said slit valve substantially equidistant from each localized hinge site.

11. A multi-lumen catheter according to claim 8 wherein the lumen-defining surface means at said convergence comprise a lumen corner surface.

12. A catheter comprising a catheter tube comprising wall means comprising inside and outside surface means, the inside surface means defining at least one asymmetrically-shaped lumen, an externally exposed slit valve disposed in the wall means normally closing the distal end of the lumen, the slit valve comprising a slit, valve wall means adjacent the slit, and a hinge means comprising a region of reduced thickness disposed at the convergence of the valve wall means, the catheter wall means and lumen-defining surface means.

13. A catheter according to claim 12 wherein the hinge means of the slit valve disposed at a single localized site and the slit thereof is spaced from the hinge means and eccentrically disposed in said slit valve.

14. A catheter according to claim 12 wherein the slit valve comprises regions of reduced thickness disposed at two spaced localized hinge sites with the slit thereof symmetrically disposed in said slit valve substantially equidistant from each localized hinge site.

15. A catheter according to claim 12 wherein the lumen-defining surface means at said convergence comprise a lumen corner surface.

16. An indwelling multi-lumen catheter comprising:
a catheter tube made of biocompatible material, the catheter tube comprising a distal end portion having a single smooth exterior surface and ending in a closed distal tip, a proximal end portion, and wall means defining a plurality of independently usable lumens extending substantially the entire length of the catheter tube;

a normally sealed, selectively operable, laterally disposed, three-position slit valve communicating between the distal end of one of the lumens and the exterior surface of the distal end portion, the slit valve affording selective influent and effluent flow control into and out of the lumen associated therewith;

the slit valve comprising a slit extending through the wall, the slit being essentially parallel to and offset from the axis of the catheter tube and being defined by opposed, aligned, normally sealed, parallel first and second edges of respective oppositely disposed first and second slit valve wall segments of the wall between the associated lumen and the exterior surface of the distal end portion, the first slit valve wall segment being pivotably displaceable inwardly and outwardly responsive to predetermined liquid pressure differentials between the pressure in the associated lumen and the pressure exterior to the catheter tube, thereby to pivot the first edge into a spaced-apart spatial relationship from the second edge, whereby the first edge is capable of selectively opening either outwardly from the normally sealed position to infuse fluid from the one of the lumens into the space exterior to the distal end portion, or inwardly from the normally sealed position to withdraw fluid from the space exterior to the distal end portion into the one of the lumens, the first slit valve wall segment comprising a chemically softened region in the material from which the first slit valve wall segment is comprised.

17. An indwelling multi-lumen catheter comprising:
a catheter tube made of biocompatible material, the catheter tube comprising a distal end portion having a single smooth exterior surface and ending in a closed distal tip, a proximal end portion, and wall means defining a plurality of independently usable lumens extending substantially the entire length of the catheter tube;

a normally sealed, selectively operable, laterally disposed, three-position slit valve communicating between the distal end of one of the lumens and the exterior surface of the distal end position, the slit valve affording selective influent and effluent flow control into and out of the lumen associated therewith;

the slit valve comprising a slit extending through the wall, the slit being essentially parallel to and offset from the axis of the catheter tube and being defined by opposed, aligned, normally sealed, parallel first and second edges of respective oppositely disposed first and second slit valve wall segments of the wall between the associated lumen and the exterior surface of the distal end portion, the first slit valve wall segment being pivotably displaceable inwardly and outwardly responsive to predetermined liquid pressure differentials between the pressure in the associated lumen and the pressure exterior to the catheter tube, thereby to pivot the first edge into a spaced-apart spatial relationship from the second edge, whereby the first edge is capable of selectively opening either outwardly from the normally sealed position to infuse fluid from the one of the lumens into the space exterior to the distal end portion, or inwardly from the normally sealed position to withdraw fluid from the space exterior to the distal end portion into the one of the lumens, the first slit valve wall segment comprising a region of enhanced flexibility in the material from which the first slit valve wall segment is comprised.

18. An indwelling multi-lumen catheter comprising:
a catheter tube made of biocompatible material, the catheter tube comprising a distal end portion having a single smooth exterior surface and ending in a closed distal tip, a proximal end portion, and wall means defining a plurality of independently usable lumens extending substantially the entire length of the catheter tube;

a normally sealed, selectively operable, laterally disposed, three-position slit valve communicating between the distal end of one of the lumens and the exterior surface of the distal end portion, the slit valve affording selective influent and effluent flow control into and out of the lumen associated therewith;

the slit valve comprising a slit extending through the wall, the slit being essentially parallel to and offset from the axis of the catheter tube and being defined by opposed, aligned, normally sealed, parallel first and second edges of respective oppositely disposed first and second slit valve wall segments of the wall between the associated lumen and the exterior surface of the distal end portion, the first slit valve wall segment being pivotably displaceable inwardly and outwardly responsive to predetermined liquid pressure differentials between the pressure in the associated lumen and the pressure exterior to the catheter tube, thereby to pivot the first edge into a spaced-apart spatial relationship from the second edge, whereby the first edge is capable of selectively opening either outwardly from the normally sealed position to infuse fluid from the one of the lumens into the space exterior to the distal end portion, or inwardly from the normally sealed position to withdraw fluid from the space exterior to the distal end portion into the one of the lumens, the first slit valve wall segment comprises a relatively thin localized site in the material from which the first slit valve wall segment is comprised.

19. An indwelling catheter comprising a catheter tube having at least one internal lumen formed in the distal end portion thereof, the distal end of the lumen being separated from the exterior of the catheter tube by a wall segment through which is formed a normally closed slit valve, the slit valve comprising a slit formed through the wall segment and a first three-position hinge defined by a localized reduced thickness region in the wall segment located in a spaced relationship to the slit.

20. An indwelling catheter as recited in claim 19, further comprising a second three-position hinge defined by a localized reduced thickness region in the wall segment in space relationship to the slit and located in the wall segment in symmetrical relationship to the first hinge from the slit.

21. A multi-lumen, valved catheter comprising:
a flexible tube having formed longitudinally therewithin a plurality of fluid flow lumens, a first of the lumens being capable of communication at the distal end thereof with the exterior of the tube through a slit valve biased into a closed position precluding the communication and selectively operable therefrom into either an inwardly or an outwardly open position, the slit valve comprising:

(a) a slit in the outer wall of the tube extending from the exterior thereof to the first of the lumens, the opposite first and second sides of the slit being sealingly engaged with each other in the closed position of the slit valve;

(b) a first slit valve wall comprising a portion of the outer wall of the tube adjacent the first side of the slit, the first slit valve wall being flexible selectively inwardly into the first of the lumens in the inwardly open position of the slit valve or outwardly toward the exterior of the tube in the outwardly open position of the slit valve; and (c) a first hinge means located at a side of the first valve wall remote from the slit for concentrating flexing of the first hinge wall into either the inwardly or the outwardly open positions of the slit valve.

22. A multi-lumen, valved catheter as recited in claim 21, wherein the first slit valve wall at the slit is at least as thick as at the first hinge means.

23. A multi-lumen, valved catheter as recited in claim 22, wherein the first slit valve wall at the slit is thicker than at the first hinge means.

24. A multi-lumen, valved catheter as recited in claim 21, wherein the first hinge means comprises a first region at a side of the first slit valve wall remote from the slit having enhanced flexibility relative to the portion of the first slit valve wall between the first region and the slit.

25. A multi-lumen, valved catheter as recited in claim 24, wherein the first region is chemically softened.

26. A multi-lumen, valved catheter as recited in claim 24, wherein the first region is thinner than the portion of the first slit valve wall between the first hinge means and the slit.

27. A multi-lumen, valved catheter as recited in claim 26, wherein opposite sides of the first region avoid contact with each other in the closed position of the slit valve.

28. A multi-lumen, valved catheter as recited in claim 21, wherein the first hinge means comprises a localized region of reduced thickness in the outer wall of the tube at a side of the first slit valve wall remote from the slit.

29. A multi-lumen, valved catheter as recited in claim 21, wherein the slit is disposed generally parallel to the longitudinal axis of the tube.

30. A multi-lumen, valved catheter as recited in claim 21, wherein the first hinge means comprises a region remote from the slit and parallel thereto having enhanced flexibility relative to the portion of the first slit valve wall between the region of reduced flexibility and the slit.

31. A multi-lumen, valved catheter as recited in claim 21, wherein the exterior cross-section of the tube at the distal end thereof is circular.

32. A multi-lumen, valved catheter as recited in claim 21, wherein the periphery of the cross-section of the first of the lumens comprises a corner, and the corner is closer to the outer surface of the tube than any other portion of the periphery proximate to the corner.

33. A multi-lumen, valved catheter as recited in claim 32, wherein the corner coincides with the first hinge means.

34. A multi-lumen, valved catheter as recited in claim 32, wherein the cross-section of the first of the lumens is D-shaped.

35. A multi-lumen, valved catheter as recited in claim 34, wherein the first region comprises a corner of the periphery of the cross-section of the first of the lumens, the corner being closer to the outer surface of the tube than any other portions of the periphery proximate to the corner.

36. A multi-lumen, valved catheter as recited in claim 21, wherein the first slit valve wall flexes into the inwardly open position of the slit valve when the pressure outside the tube exceeds the pressure inside the first of the lumens by a predetermined withdrawal threshold.

37. A multi-lumen, valved catheter as recited in claim 36, wherein the catheter is usable in the cardiovascular system of a patient and wherein the withdrawal threshold exceeds the systolic pressure in the circulatory system of the patient.

38. A multi-lumen, valved catheter as recited in claim 36, wherein the first slit valve wall flexes into the outwardly open position of the slit valve when the pressure inside the first of the lumens exceeds the pressure outside the tube by a predetermined infusion threshold.

39. A multi-lumen, valved catheter as recited in claim 38, wherein the catheter is usable in the cardiovascular system of a patient, and wherein the infusion threshold exceeds the pressure arising from the venturi effect of blood flowing in the circulatory system of the patient at the distal end of the catheter.

40. A multi-lumen, valved catheter as recited in claim 38, wherein the withdrawal threshold exceeds the infusion threshold.

41. A multi-lumen, valved catheter as recited in claim 38, wherein the infusion threshold exceeds the withdrawal threshold.

42. A multi-lumen, valved catheter as recited in claim 21, wherein the slit valve further comprises:

(a) a second slit valve wall comprising a portion of the outer wall of the tube adjacent the second side of the slit, the second slit valve wall being flexible selectively inwardly into the first of the lumens in the inwardly open position of the slit valve or outwardly toward the exterior of the tube in the outwardly open position of the slit valve; and (b) a second hinge means located at a side of the second valve wall remote from the slit for concentrating flexing of the second hinge wall into either the inwardly or the outwardly open positions of the slit valve.

43. A multi-lumen, valved catheter as recited in claim 42, wherein the first and second hinge means are parallel to the slit.

44. A multi-lumen, valved catheter as recited in claim 42, wherein the first and second slit valve walls at the slit are at least as thick as the first and second slit valve walls, at the first and second hinge means, respectively.

45. A multi-lumen, valved catheter as recited in claim 44, wherein the first and second hinge walls at the slit are thicker than at the first and second hinge means, respectively.

46. A multi-lumen, valved catheter as recited in claim 44, wherein the periphery of the cross section of the first of the lumens comprises a curved section generally concentric with the outer surface of the tube, the curved section being closer to the outer surface of the tube than any other portion of the periphery of the cross section proximate to the curved portion.

47. A multi-lumen, valved catheter as recited in claim 42, wherein the first and second hinge means each comprises first and second regions at the sides of the first and second hinge walls, respectively, remote from the slit having enhanced flexibility relative to the part of the first and second hinge walls, respectively, between the first and second regions and the slit.

48. A multi-lumen, valved catheter as recited in claim 47, wherein the first and second regions each comprise a corner of the periphery of the cross-section of the first of the lumens that is closer to the outer surface of the tube than any other portions of the periphery of the cross-section of the first of the lumens.

49. A multi-lumen, valved catheter as recited in claim 42, wherein the first and second hinge means each comprises localized regions of reduced thickness in the outer wall of the tube at opposite sides of the first and the second slit valve walls, respectively, remote from the slit.

50. A multi-lumen, valved catheter as recited in claim 42, wherein the periphery of the cross-section of the first of the lumens comprises a first and a second corner, and the first and second corners are closer to the outer surface of the tube than any other portions of the periphery of the cross-section proximate to the first and second corners.

51. A multi-lumen, valved catheter as recited in claim 50, wherein the first and second corners coincide with the first and second hinge means, respectively.

52. A multi-lumen, valved catheter as recited in claim 50, wherein the cross-section of the first of the lumens, is D-shaped.

53. A multi-lumen, valved catheter comprising:
a flexible tube having formed longitudinally therewithin a plurality of fluid flow lumens, each of the lumens being independently capable of communication at the distal end thereof with the exterior of the tube through a slit valve biased into a closed position precluding the communication and selectively openable therefrom into either an inwardly or an outwardly open position, each of the slit valves comprising:
  (a) a slit in the outer wall of the tube extending from the exterior thereof to the lumen, the opposite first and second sides of the slit being sealingly engaged with each other in the closed position of the slit valve;
  (b) a first slit valve wall comprising a portion of the outer wall of the tube adjacent the first side of the slit, the first slit valve wall being flexible selectively inwardly into the first of the lumens in the inwardly open position of the slit valve or outwardly toward the exterior of the tube in the outwardly open position of the slit valve; and
  (c) a first hinge means located at a side of the first valve wall remote from the slit for concentrating flexing of the first hinge wall into either the inwardly or the outwardly open positions of the slit valve.

54. A multi-lumen, valved catheter as recited in claim 53, wherein each of the slit valves further comprises:
  (a) a second slit valve wall comprising a portion of the outer wall of the tube adjacent the second side of the slit, the second slit valve wall being flexible selectively inwardly into the lumens in the inwardly open position of the slit valve or outwardly toward the exterior of the tube in the outwardly open position of the slit valve; and
  (b) a second hinge means located at a side of the second valve wall remote from the slit for concentrating flexing of the second hinge wall into either the inwardly or the outwardly open positions of the slit valve.

55. A single-lumen valved catheter comprising:
a flexible tube having formed longitudinally therewithin a fluid flow lumen capable of communication at the distal end thereof with the exterior of the tube through a slit valve biased into a closed position precluding the communication and selectively openable therefrom into either an inwardly or an outwardly open position, the slit valve comprising:
  (a) a slit in the outer wall of the tube extending from the exterior thereof to the lumen, the opposite first and second sides of the slit being sealingly engaged with each other in the closed position of the slit valve;
  (b) a first slit valve wall comprising a portion of the outer wall of the tube adjacent the first side of the slit, the first slit valve wall being flexible selectively inward into the lumen in the inwardly open position of the slit valve or outwardly toward the exterior of the tube in the outwardly open position of the slit valve; and
  (c) a first hinge means located at a side of the first valve wall remote from the slit for concentrating flexing of the first hinge wall into either the inwardly or the outwardly open positions of the slit valve.

56. A single-lumen, valved catheter as recited in claim 55, wherein the slit valve further comprises:
  (a) a second slit valve wall comprising a portion of the outer wall of the tube adjacent the second side of the slit, the second slit valve wall being flexible selectively inwardly into the lumen in the inwardly open position of the slit valve or outwardly toward the exterior of the tube in the outwardly open position of the slit valve; and
  (b) a second hinge means located at a side of the second valve wall remote from the slit for concentrating flexing of the second hinge wall into either the inwardly or the outwardly open positions of the slit valve.

* * * * *